US012682138B2

(12) United States Patent
Ona et al.

(10) Patent No.: US 12,682,138 B2
(45) Date of Patent: Jul. 14, 2026

(54) ADHESION PREDICTION METHOD, ADHESION PREDICTION PROGRAM, AND ADHESION PREDICTION DEVICE

(71) Applicant: TOYOTA JIDOSHA KABUSHIKI KAISHA, Toyota (JP)

(72) Inventors: Kunihito Ona, Toyota (JP); Kazuhiro Suzuki, Miyoshi (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 1332 days.

(21) Appl. No.: 17/480,775

(22) Filed: Sep. 21, 2021

(65) Prior Publication Data

US 2022/0198104 A1 Jun. 23, 2022

(30) Foreign Application Priority Data

Dec. 23, 2020 (JP) ................................. 2020-213224

(51) Int. Cl.
| | |
|---|---|
| *G06F 30/25* | (2020.01) |
| *G01N 33/20* | (2019.01) |
| *G06F 30/20* | (2020.01) |
| *G06F 113/22* | (2020.01) |
| *G06F 119/18* | (2020.01) |

(52) U.S. Cl.
CPC ............. *G06F 30/25* (2020.01); *G01N 33/20* (2013.01); *G06F 30/20* (2020.01); *G06F 2113/22* (2020.01); *G06F 2119/18* (2020.01)

(58) Field of Classification Search
CPC ...... G06F 30/25; G06F 30/20; G06F 2119/18; G06F 2113/22; G01N 33/20
See application file for complete search history.

(56) References Cited

U.S. PATENT DOCUMENTS

2019/0085464 A1 3/2019 Miyasaka

FOREIGN PATENT DOCUMENTS

| GB | 2566831 A | * 3/2019 | ............. G06F 30/15 |
|---|---|---|---|
| JP | 2015-199098 A | 11/2015 | |
| JP | 2017-206762 A | 11/2017 | |

OTHER PUBLICATIONS

Wujiao Xu, NPL, "Experimental and theoretical analysis of wear mechanism in hot-forging die and optimal design of die geometry", Published Jun. 30, 2014 (Year: 2014).*

(Continued)

*Primary Examiner* — Rehana Perveen
*Assistant Examiner* — Angel Calle
(74) *Attorney, Agent, or Firm* — Sughrue Mion, PLLC

(57) ABSTRACT

An adhesion prediction method of predicting adhesion of metal particles in a workpiece to a die in a forging process using an aluminum-based material as the workpiece includes: a cumulative friction work amount calculation step of calculating a cumulative friction work amount generated between the workpiece and the die; a metal diffusion analysis step of analyzing a diffusion state of the metal particles between the workpiece and the die; and an adhesion prediction determination step of predicting a state of occurrence of the adhesion of the metal particles to the die, considering the cumulative friction work amount calculated in the cumulative friction work amount calculation step, the diffusion state analyzed in the metal diffusion analysis step, and a film thickness of a lubricating film provided on a surface of the die that comes into contact with the workpiece.

12 Claims, 5 Drawing Sheets

(56) References Cited

OTHER PUBLICATIONS

Hyunok Kim, NPL, "Prediction and Elimination of Galling in Forming Galvanized Advanced High Strength Steels (AHSS)", Published 2008 (Year: 2008).*

* cited by examiner

FIG. 6

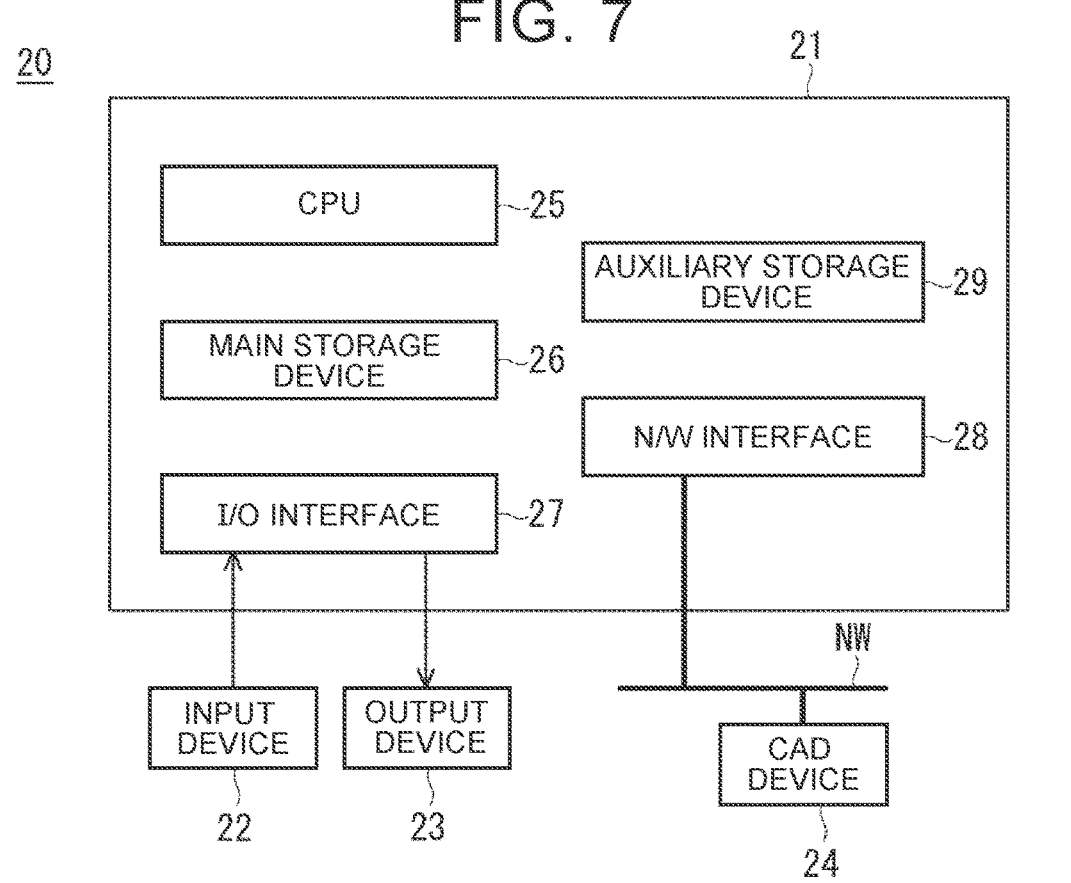

<1> OXIDE FILM/ LUBRICATING FILM REMAINING PERIOD

<2> WORKPIECE/ DIE CONTACT PERIOD

INFLUENCE OF SURFACE PRESSURE/SLIDING DISTANCE IS DOMINANT

INFLUENCE OF WORKPIECE/DIE TEMPERATURE IS DOMINANT

ADHESION DETERMINATION FUNCTION VALUE $E_{adhesion}$ (2)

ADHESION OCCURRENCE PREDICTION THRESHOLD VALUE T (1)

FORGING PROGRESS TIME t

CPU ~25

AUXILIARY STORAGE DEVICE ~29

MAIN STORAGE DEVICE ~26

N/W INTERFACE ~28

I/O INTERFACE ~27

NW

INPUT DEVICE

OUTPUT DEVICE

CAD DEVICE

22

23

24

ADHESION PREDICTION METHOD, ADHESION PREDICTION PROGRAM, AND ADHESION PREDICTION DEVICE

CROSS-REFERENCE TO RELATED APPLICATION

This application claims priority to Japanese Patent Application No. 2020-213224 filed on Dec. 23, 2020, incorporated herein by reference in its entirety.

BACKGROUND

1. Technical Field

The present disclosure relates to an adhesion prediction method, an adhesion prediction program, and an adhesion prediction device for aluminum or an aluminum alloy (collectively referred to as "aluminum" in the present specification) with respect to a die.

2. Description of Related Art

As a method for forming a metal product, there is a method of forming a workpiece (material to be processed) through a forging process using a die. Japanese Unexamined Patent Application Publication No. 2015-199098 (JP 2015-199098 A) discloses an adhesion prediction method for an aluminum-plated steel sheet for a case in which no lubricating oil is used. More specifically, JP 2015-199098 A discloses a prediction method including: an analysis step of obtaining an analysis of a temperature distribution, a surface pressure distribution, and an in-plane compressive stress distribution of a steel sheet in the processes of press forming and cooling during hot stamping, with a combination of thermal analysis and structural analysis; a result processing step of calculating a distribution of a product of the surface pressure and the in-plane compressive stress based on the analyses; and a determination processing step of determining a state of occurrence of adhesion of aluminum plating to a die during the hot stamping based on the distribution of the product.

SUMMARY

In recent years, due to a demand for weight reduction of vehicle bodies, importance of the forming technology with a forging process using as a workpiece an aluminum-based material including aluminum or an aluminum alloy (hereinafter also referred to as aluminum forging process) is increasing, in addition to the forming technology using a steel sheet as a workpiece as in JP 2015-199098 A. However, since aluminum is a soft material, there is an issue that metal particles in the workpiece tend to adhere to the die in the aluminum forging process.

When the metal particles in the workpiece adhere to the die, it is necessary to remove the adhered aluminum or replace the die. In addition, poor quality of the formed product due to the adhesion of metal particles to the die may become a problem. It takes a lot of man-hours for die maintenance measures and adjustment of conditions of the lubricating film in order to reduce such a situation, which causes problems of decrease in productivity and increase in cost. If it is possible to predict the adhesion of metal particles in the workpiece to the die in advance, it is possible to take measures such as optimizing the manufacturing process, which can realize improvement in the productivity of forged aluminum parts and improvement in quality of the formed products.

The present disclosure has been made in view of the above circumstances, and provides an adhesion prediction method, an adhesion prediction program, and an adhesion prediction device for predicting adhesion of metal particles to a die in an aluminum forging process.

A first aspect of the present disclosure relates to an adhesion prediction method of predicting adhesion of metal particles in a workpiece to a die in a forging process using an aluminum-based material as the workpiece. The adhesion prediction method includes: a cumulative friction work amount calculation step of calculating a cumulative friction work amount generated between the workpiece and the die; a metal diffusion analysis step of analyzing a diffusion state of the metal particles between the workpiece and the die; and an adhesion prediction determination step of predicting a state of occurrence of the adhesion of the metal particles to the die, considering the cumulative friction work amount calculated in the cumulative friction work amount calculation step, the diffusion state analyzed in the metal diffusion analysis step, and a film thickness of a lubricating film provided on a surface of the die that comes into contact with the workpiece.

With the above configuration, in the aluminum forging process, the occurrence of adhesion of the metal particles to the die can be predicted in advance from the processing shape, lubrication conditions, and the like. As a result, improvement in productivity and quality in the aluminum forging process can be realized.

Preferable examples of the adhesion prediction determination step include a method including performing a computing process of computing a product of a term obtained by dividing a function of the cumulative friction work amount by the film thickness of the lubricating film and a term of a function of the diffusion state, and determining a prediction of the occurrence of the adhesion of the metal particles to the die considering a result of the computing process.

Preferable examples of the calculation method of the cumulative friction work amount include a method in which the cumulative friction work amount is calculated from a function obtained by integrating, over a forging time, a contact surface pressure, a friction coefficient, and a sliding velocity acting between the workpiece and the die for a minute time at each of element parts of the workpiece and the die.

Preferable examples of the analysis method of the diffusion state include a method including analyzing a diffusion amount of the metal particles using the Arrhenius equation in consideration of a combination of materials of the workpiece and the die and a processing temperature.

A second aspect of the present disclosure relates to an adhesion prediction program for predicting adhesion of metal particles in a workpiece to a die in a forging process using an aluminum-based material as the workpiece. The adhesion prediction program causes a computer to execute: a cumulative friction work amount calculation process of calculating a cumulative friction work amount generated between the workpiece and the die; a metal diffusion analysis process of analyzing a diffusion state of the metal particles between the workpiece and the die; and an adhesion prediction determination process of predicting a state of occurrence of the adhesion of the metal particles to the die, considering the cumulative friction work amount calculated in the cumulative friction work amount calculation process, the diffusion state analyzed in the metal diffusion analysis process, and a film thickness of a lubricating film provided on a surface of the die that comes into contact with the workpiece. With the above configuration, in the aluminum forging process, the occurrence of adhesion of the metal particles to the die can be predicted in advance from the product shape, lubrication conditions, and the like. As a result, improvement in productivity and quality in the aluminum forging process can be realized.

A third aspect of the present disclosure relates to an adhesion prediction device for predicting adhesion of metal particles in a workpiece to a die in a forging process using an aluminum-based material as the workpiece. The adhesion prediction device includes: a cumulative friction work amount calculation unit that calculates a cumulative friction work amount generated between the workpiece and the die; a metal diffusion analysis unit that analyzes a diffusion state of the metal particles between the workpiece and the die; and an adhesion prediction determination unit that predicts a state of occurrence of the adhesion of the metal particles to the die, considering the cumulative friction work amount calculated by the cumulative friction work amount calculation unit, the diffusion state analyzed by the metal diffusion analysis unit, and a film thickness of a lubricating film provided on a surface of the die that comes into contact with the workpiece. With the above configuration, in the aluminum forging process, the occurrence of adhesion of the metal particles to the die can be predicted in advance from the product shape, lubrication conditions, and the like. As a result, improvement in productivity and quality in the aluminum forging process can be realized.

According to the present disclosure, it is possible to provide an adhesion prediction method, an adhesion prediction program, and an adhesion prediction device for predicting adhesion of metal particles to a die in an aluminum forging process.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 6 is a graph showing an example of an adhesion determination function with respect to a forging progress time in the adhesion prediction method of the present embodiment;

FIG. 7 is a block diagram showing an example of a hardware configuration of an adhesion prediction device of the present embodiment.

DETAILED DESCRIPTION OF EMBODIMENTS

Hereinafter, an example of the present embodiment will be described, but the disclosure according to the claims is not limited to the following embodiments. Also, not all of the configurations described in the embodiments are indispensable as means for solving the problem. For the sake of clarity, the following description and drawings have been omitted and simplified as appropriate.

Before describing the present disclosure through the embodiments of the present disclosure, first, adhesion of metal particles in the workpiece to a die in an aluminum forging process will be described with reference to FIGS. 1 to 4. Note that aluminum-based material herein represents aluminum or an aluminum alloy. The aluminum alloy refers to an alloy containing iron, silicon, copper, zinc, magnesium, manganese, chromium, titanium or/and nickel in addition to aluminum (Al) and unavoidable impurities. The metal particles to adhere are of metals derived from the components of the workpiece, and herein, of metals derived from the components of aluminum or an aluminum alloy.

Figure 1:
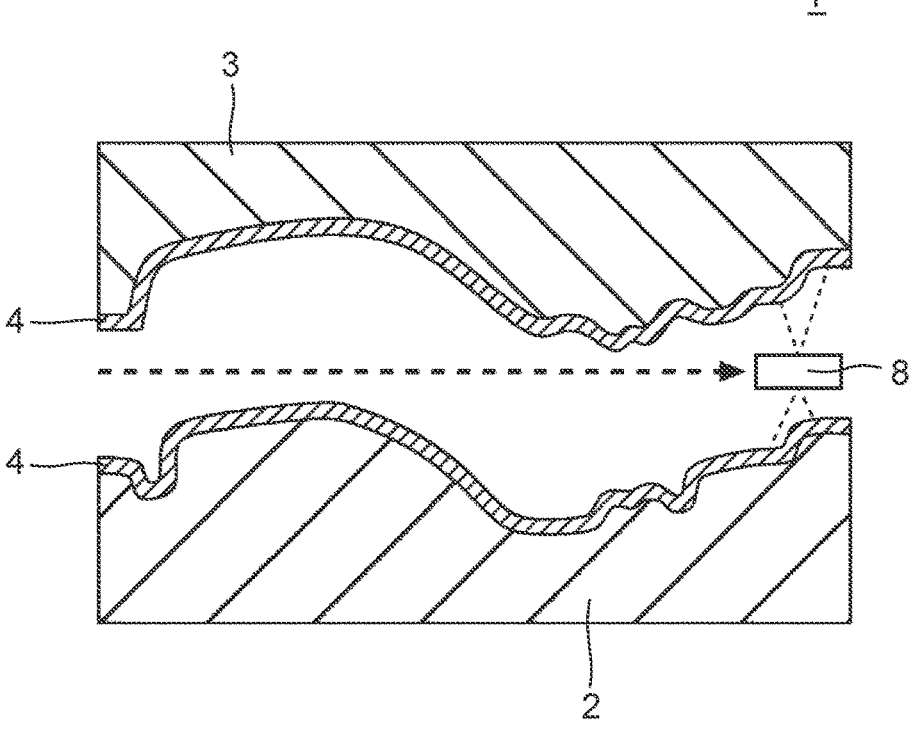
FIG. 1 is a schematic diagram illustrating a manufacturing process of an aluminum forging process.

As shown in FIG. 1, a forging apparatus 1 has a lower die 2 and an upper die 3 that are arranged so as to be separated from each other and face each other and that function as a set of dies. A lubricating film 4 is provided on each processing surface of the lower die 2 and the upper die 3 which comes into contact with the workpiece. The lubricating film 4 may be formed by any method, and a known method can be adopted. In the example of FIG. 1, the lubricating film 4 is formed by applying a lubricant (release agent) to the processing surface using a lubricant application device 8 that is movable with respect to the processing surface. The lubricant may be applied at any timing. There are methods of applying the lubricant for each workpiece or after manufacturing a fixed number of workpieces. The lubricating film 4 has a role of facilitating the release of the workpiece from the die after the forging process and suppressing the adhesion of metal particles in the workpiece to the die. To the die, another layer such as a base layer may be optionally provided in addition to the lubricating film, or surface treatment may be performed.

Figure 2:
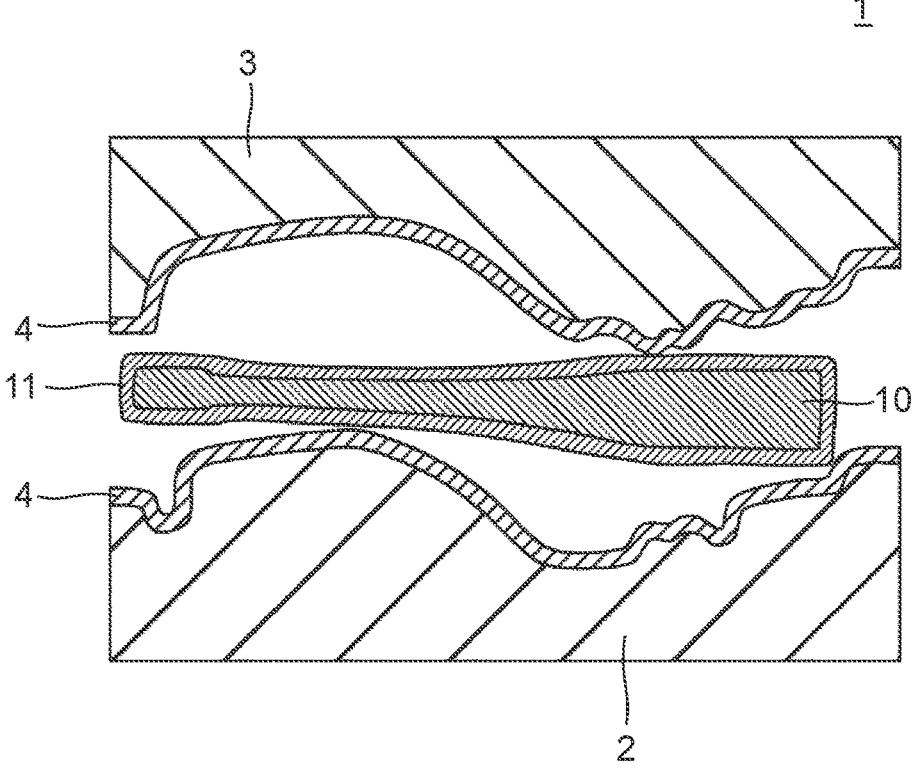
FIG. 2 is a schematic diagram illustrating the manufacturing process of the aluminum forging process.

As shown in FIG. 2, a workpiece 10 made of an aluminum-based material is set in the forging apparatus 1. An oxide film 11 is usually provided on the surface of the workpiece 10. The oxide film 11 may change depending on the components of the material to be processed. Further, the state of the oxide film 11 including the film thickness may change depending on a temperature history, a heating amount, a surface treatment method, and the like of the workpiece 10. The workpiece 10 may be further surface-treated.

Figure 3:
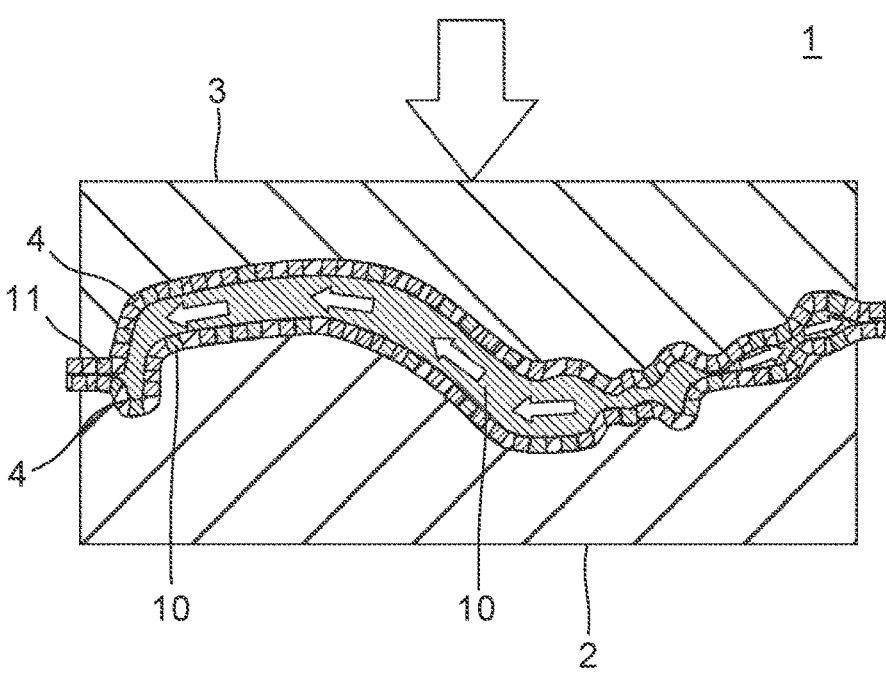
FIG. 3 is a schematic diagram illustrating the manufacturing process of the aluminum forging process.
Figure 4:
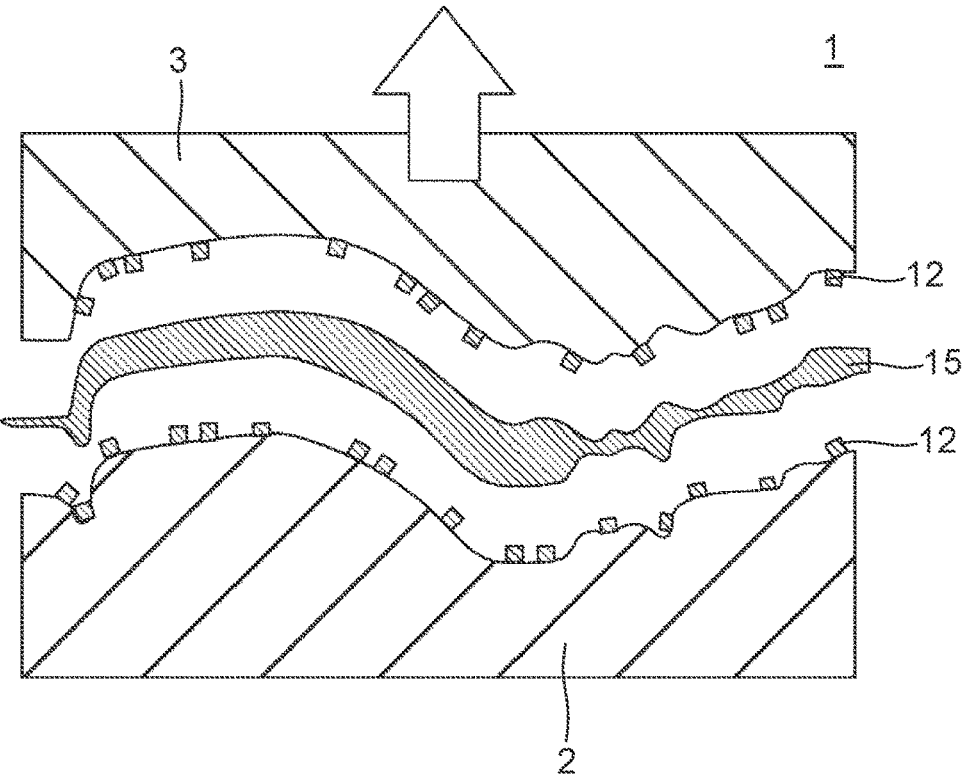
FIG. 4 is a schematic diagram illustrating the manufacturing process of the aluminum forging process.

Next, as shown in FIG. 3, a forging process is performed in which a predetermined pressure and, if necessary, heat are applied to the lower die 2 and the upper die 3 (hereinafter, also collectively referred to as the lower die 2 and the like) to deform the workpiece 10. Then, as shown in FIG. 4, the pressing of the lower die 2 and the upper die 3 is released to obtain a forged product 15. In the example shown in FIG. 4, adhesion of metal particles 12 derived from the components of the workpiece 10 is observed on contact surfaces of the lower die 2 and the like with respect to the workpiece 10.

The presence of the lubricating films 4 on the processing surfaces of the lower die 2 and the like (see FIG. 1) and the oxide film 11 of the workpiece 10 (see FIG. 2) has an effect of suppressing the adhesion of metal particles in the aluminum forging process. However, as the forging progress time elapses, the lubricating film 4 and the oxide film 11 become thinner independently, and finally the lubricating film 4 and the oxide film 11 break during forming, and a fresh surface inside the workpiece 10 and the base material of the lower die 2 and the like come into contact with each other. This contact causes a reaction between the components of the dies and the components of the workpiece, thereby forming a metal bonding. It is considered that when the workpiece 10 is taken out from the lower die 2 and the like, the metal particles in the workpiece adhere to the surfaces of the lower die 2 and the like due to the metal bonding.

As a factor of adhesion of metal particles to a die in the aluminum forging process, metal bonding (diffusion state) due to a reaction between the materials of the die and the workpiece is conceivable. Further, the condition that the lubricating film of the die and the oxide film (surface-treated state) of the workpiece are broken triggers the adhesion. The holding power of the lubricating film can vary depending on the roughness of the die surface and the adhesion amount of the lubricating film. In addition, the amount of heat-resistant components of the lubricating film used and the process temperature can affect the lubrication heat resistance. Therefore, a contact surface pressure, a sliding velocity, and a friction coefficient between the workpiece and the die are also important factors that determine the adhesion of the metal particles to the die. Furthermore, the metal bonding is affected by environmental conditions such as temperature.

Figure 5:
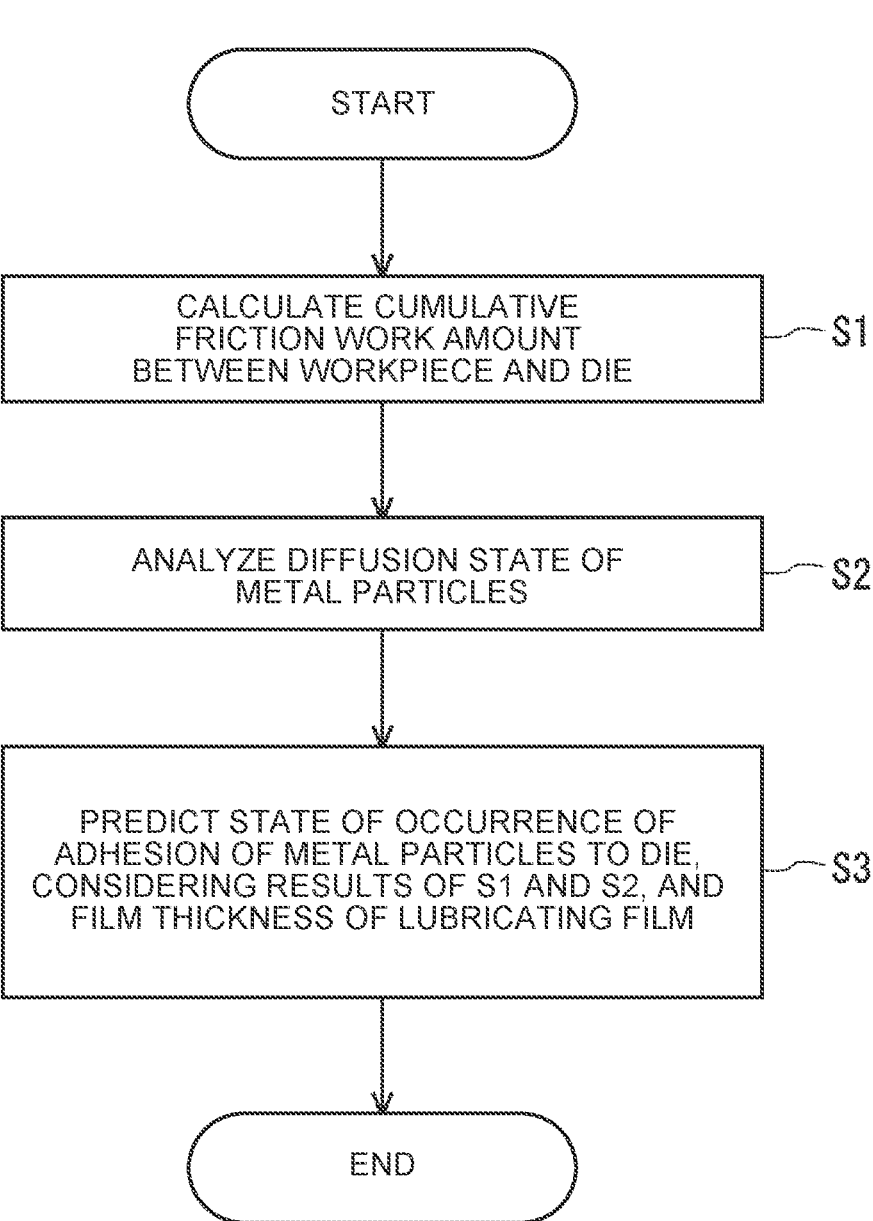
FIG. 5 is a flowchart showing an example of an adhesion prediction method of the present embodiment.

Regarding the adhesion of metal particles in the aluminum forging process, it is necessary to consider various factors as described above. As a result of diligent studies by the present inventors, it was found that the adhesion of metal particles to the die can be predicted by a method shown in FIG. 5. That is, as shown in FIG. 5, an adhesion prediction method according to the present embodiment includes: a cumulative friction work amount calculation step (S1) of calculating a cumulative friction work amount generated between a workpiece and a die; a metal diffusion analysis step (S2) of analyzing a diffusion state of the metal particles between the workpiece and the die; and an adhesion prediction determination step (S3) of predicting a state of occurrence of adhesion of the metal particles to the die, considering the cumulative friction work amount calculated in the cumulative friction work amount calculation step (S1), the diffusion state analyzed in the metal diffusion analysis step (S2), and a film thickness of a lubricating film provided on a surface of the die that comes into contact with the workpiece. The cumulative friction work amount calculation step (S1) and the metal diffusion analysis step (S2) may be performed in any order, and the steps may be performed at the same time.

Examples of the adhesion prediction determination step (S3) includes a method in which a computing process is performed to compute a product of the term obtained by dividing a function of the cumulative friction work amount by the film thickness of the lubricating film and the term of a function of the diffusion state, and an adhesion occurrence prediction for the metal particles to the die is determined.

Main factors of the cumulative friction work amount between the workpiece and the die calculated in the cumulative friction work amount calculation step (S1) are a friction coefficient and a sliding velocity mainly based on the contact surface pressure between the die and the workpiece corresponding to the deformation resistance of the workpiece, the die surface roughness, and the like. In one processing as a whole, the cumulative friction work amount obtained by integrating the friction work with the entire processing is generated. Values of the contact surface pressure, the friction coefficient, and the sliding velocity change depending on the states of the lubricating film and the oxide film. The type and the film thickness of the lubricating film are important factors that determine the cumulative friction work amount.

The cumulative friction work amount Ef can be calculated from a function obtained by integrating the contact surface pressure, the friction coefficient, and the sliding velocity acting between the workpiece and the die in a minute time at each element part of the workpiece and the die over the forging time. For example, the cumulative friction work amount Ef can be calculated by the following equation (1) in which a frictional force acting between the workpiece and the die ($\mu$P, where $\mu$ is the friction coefficient and P is the contact surface pressure) is multiplied by the slip distance and the result is integrated over one forging period.

$$Ef = \int \mu P v dt \qquad \text{equation (1)}$$

In equation (1), v is a relative sliding velocity.

The diffusion state of the metal particles between the workpiece and the die analyzed in the metal diffusion analysis step (S2) can change depending on the combination of the components of the workpiece and the die. Diffusion is caused by metal bonding through a chemical reaction due to the contact between the two. It is also affected by processing conditions such as the temperature of the forging process. Taking these into consideration, the diffusion state of the metal particles is analyzed.

The diffusion state (diffusion amount) of the metal particles is obtained by performing the analysis using the Arrhenius equation in consideration of the combination of the materials of the workpiece and the die and the processing temperature. For example, the diffusion state can be obtained by the Arrhenius equation of diffusion. The diffusion state can be obtained by integrating the following equation as the Arrhenius equation of diffusion over one forging period.

$$D = D_0 \exp(-Q/(RT))$$

That is, the diffusion state (diffusion amount) D over one forging period can be expressed by the following equation (2).

$$D = \int D_0 \exp(-Q/(RT)) \qquad \text{equation (2)}$$

Here, D is the diffusion amount, $D_0$ is the diffusion coefficient, Q is the activation energy, R is the gas constant, and T is the temperature (K). The diffusion coefficient $D_0$ and the activation energy Q are mainly determined by the combination of the materials of the workpiece and the die.

In the adhesion prediction determination step (S3), the state of occurrence of adhesion of metal particles to the die is predicted based on the obtained cumulative friction work amount and diffusion state and the film thickness of the lubricating film provided on the surface of the die.

Examples of the function in the adhesion prediction determination step of the present embodiment include the following equation (3).

$$E_{adhesion} = \frac{F(E_f)}{L_{th}} \times \left( F\left( \int D_0 \exp(-Q/(R \cdot T)) \right) \right) \qquad \text{equation (3)}$$

In equation (3), $E_f$ is as defined in equation (1), and $\int D_0 \exp(-Q/(RT))$ is as defined in equation (2). Further, $L_{th}$ is the initial film thickness of the lubricating film.

FIG. 6 shows a typical example of the profile of an adhesion determination function $E_{adhesion}$ of the above equation (3) with respect to the forging progress time during one forging process. The graph (1) in FIG. 6 represents an example in which adhesion of metal particles is not expected in the aluminum forging process. The graph (2) in FIG. 6 represents an example in which adhesion of metal particles is expected in the aluminum forging process.

In the adhesion determination function $E_{adhesion}$ of FIG. 6, when the value exceeds an adhesion occurrence prediction threshold value T of the Y-axis, the occurrence of adhesion of metal particles to the die is predicted. The adhesion occurrence prediction threshold value T can vary depending on the types of the workpiece and the die used, the manufacturing conditions, the processing shape, and the like.

As shown in FIG. 6, the aluminum forging process can be divided into a period during which at least one of the oxide film and the lubricating film remains (period <1> in FIG. 6) and a period during which the workpiece and the die are in contact with each other (period <2> in FIG. 6). It is desirable that the forging process is completed in the former period, but as the forging progress time elapses, the oxide film of the workpiece and the lubricating film of the die become thinner, and the fresh surface inside the workpiece may come into contact with the die. In the forging process in which the oxide film of the workpiece and the lubricating film of the die remain, the contact surface pressure and the sliding distance between the workpiece and the die are dominant in the factors of the adhesion of the metal particles to the die. On the other hand, in the absence of the oxide film of the workpiece and the lubricating film of the die, the influence of the combination of materials of the workpiece and the die and the temperature of the forging process is dominant.

According to the adhesion prediction method of the present embodiment, the adhesion of metal particles to the die can be predicted in the aluminum forging process. Thus, the adhesion of the metal particles to the die can be predicted in advance from the product shape and the lubrication conditions. By designing the manufacturing process and the processing shape so that the adhesion occurrence prediction threshold value T is not exceeded, it is possible to effectively restrain the adhesion of metal particles in the aluminum forging process. That is, by adjusting the processing conditions such as the film thickness of the lubricating film, the type of the lubricating film, the oxide film of the workpiece, the surface treatment of the workpiece, and the temperature of the forging process based on the adhesion prediction of the present embodiment, it is possible to significantly improve productivity and quality of aluminum forging parts.

The adhesion prediction program of the present embodiment causes a computer to execute a cumulative friction work amount calculation process (a) of calculating a cumulative friction work amount between a workpiece and a die; a metal diffusion analysis process (b) of analyzing a diffusion state of metal particles between the workpiece and the die; and an adhesion prediction determination process (c) of predicting a state of occurrence of adhesion of the metal particles between the workpiece and the die, by computing the calculated cumulative friction work amount, the analyzed diffusion state, and a film thickness of a lubricating film provided on a surface of the die. The cumulative friction work amount calculation process (a) and the metal diffusion analysis process (b) can be performed in any order or at the same time.

The adhesion prediction device of the present embodiment includes: a cumulative friction work amount calculation unit (a) that calculates a cumulative friction work amount between a workpiece and a die; a metal diffusion analysis unit (β) that analyzes a diffusion state of metal particles between the workpiece and the die; and an adhesion prediction determination unit (γ) that determines a state of occurrence of adhesion between the workpiece and the die based on the calculated cumulative friction work amount, the analyzed diffusion state, and a film thickness of a lubricating film provided on a surface of the die.

FIG. 7 is block diagram showing an example of the hardware configuration of the adhesion prediction device that can be used in the adhesion prediction method of the present embodiment. An adhesion prediction device 20 shown in the FIG. 7 is a device that simulates the occurrence of adhesion in the aluminum forging process, and includes an information processing device 21 that forms an analysis model, an input device 22, and an output device 23. To the information processing device 21, a computer-aided design (CAD) device 24 is connected, in addition to the input device 22 and the output device 23, via a network NW such as a local area network (LAN). The input device 22 is composed of a keyboard, a mouse, and the like, and receives analysis conditions, various requests, and the like from a user for output to the information processing device 21. The output device 23 is composed of, for example, a liquid crystal monitor, a printer, or the like.

The information processing device 21 includes a central processing unit (CPU), a main storage device 26 composed of a random access memory (RAM) and the like, an input-output (I/O) interface 27, a network interface 28, and an auxiliary storage device 29 composed of a hard disk and the like.

The auxiliary storage device 29 stores a program for implementing various functions for forming an analysis model for adhesion occurrence prediction and analyzing the cumulative friction work amount, the diffusion state of metal particles, and the like. Each of the functions is realized when the CPU (computer) loads the program stored in the auxiliary storage device 29 into the main storage device 26 and executes the program.

Figure 8:
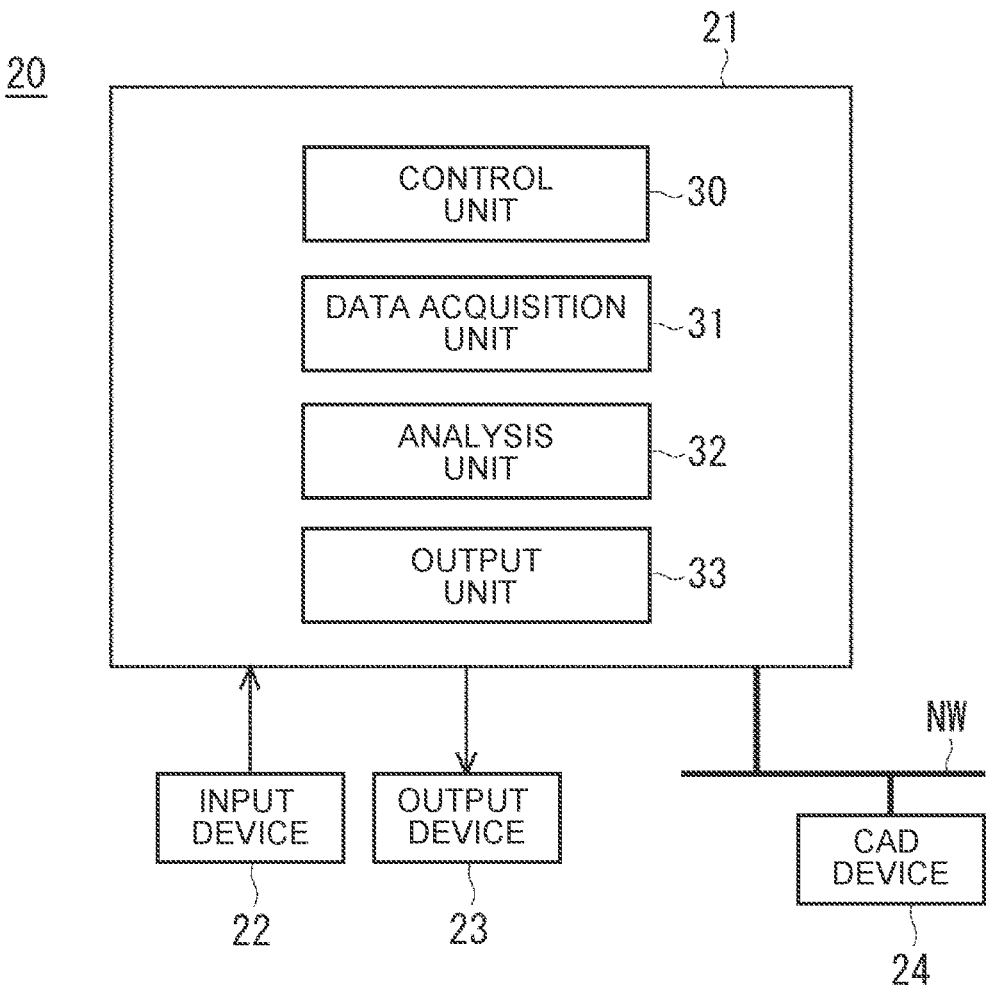
FIG. 8 is a functional block diagram showing each function performed by an information processing device of the adhesion prediction device of the present embodiment.

FIG. 8 is a functional block diagram showing each function executed by the information processing device 21. As shown in FIG. 8, the information processing device 21 includes a control unit 30, a data acquisition unit 31, an analysis unit 32, an output unit 33, and the like.

The control unit 30 controls the overall operation of the information processing device 21. The control unit 30 also receives various requests input by a designer via the input device 22. The control unit 30 controls the data acquisition unit 31, the analysis unit 32, and the output unit 33 following the received requests, and performs various processes corresponding to the requests from the designer.

In addition, the data acquisition unit 31 communicates with the CAD device 24 connected to the network NW to transmit and receive the analysis data to and from each other. For example, the data acquisition unit 31 accesses the CAD device 24 via the network NW and acquires design information (CAD information) stored in the CAD device 24. The data acquisition unit 31 receives input of various conditions that are used for analysis and input by the designer via the input device 22.

The analysis unit 32 outputs a simulation result (analysis model) of occurrence of adhesion using the design information and the analysis condition information of the aluminum forging process acquired from the CAD device 24. Also, the output unit 33 acquires the analysis result from the analysis unit 32, generates image information indicating the analysis result, and outputs the generated image information to the output device 23. The image information can be shown by a graph showing timings at which adhesion is predicted to occur, or can be indicated by a mapping diagram of the processing shape of the workpiece, for example. Further, the value of the adhesion determination function may be indicated in different colors by section on the presentation, or may be divided into segments by a threshold value to be indicated. In addition, suitable temperature conditions, the film thickness of the lubricating film, and the like may also be displayed.

According to the adhesion prediction device and the adhesion prediction program of the present embodiment, occurrence of adhesion can be predicted in advance from the combination of the workpiece and the die, the diffusion state based on manufacturing conditions, the design of formed product, and the state of mechanical load based on processing conditions (cumulative friction work amount), which cause aluminum adhesion to the die for aluminum forging. Accordingly, it is possible to easily find the conditions under which adhesion can be restrained, and thus, the productivity can be improved. Further, by restraining the adhesion of metal particles, it is possible to provide a high quality forged product.

The adhesion prediction device of the present embodiment can also be used in conjunction with the aluminum forging apparatus to predict the occurrence of adhesion in real time during manufacturing. In this case, appropriate measures are taken, for example, a warning is provided at the timing at which adhesion is predicted to occur, a lubricating film is applied to the die, and the temperature is optimized, so that it is possible to restrain the adhesion to the die. In addition, the aluminum forging apparatus may be set such that the aluminum forging apparatus stops when the occurrence of adhesion is imminent. According to such a usage, it is possible to provide adhesion prediction in consideration of delicate conditions of the apparatus or equipment at that time, thereby dramatically improving the production efficiency.

What is claimed is:

1. An adhesion prediction method of predicting an adhesion of metal particles in a workpiece to a die in a forging process using an aluminum-based material as the workpiece, the adhesion prediction method comprising:
    an input step of receiving computer aided design (CAD) information from a CAD device and various conditions that are used for analysis from an input device;
    a cumulative friction work amount calculation step of calculating a cumulative friction work amount generated between the workpiece and the die;
    a metal diffusion analysis step of analyzing a diffusion state of the metal particles between the workpiece and the die;
    an adhesion prediction determination step of predicting an occurrence of the adhesion of the metal particles to the die, considering the cumulative friction work amount calculated in the cumulative friction work amount calculation step, the diffusion state analyzed in the metal diffusion analysis step, and a film thickness of a lubricating film provided on a surface of the die that comes into contact with the workpiece, the metal particles being of the aluminum-based material; and
    an output step of outputting an analysis model of the occurrence of the adhesion.

2. The adhesion prediction method according to claim 1, wherein the adhesion prediction determination step includes:
    performing a computing process of computing a product of a first term obtained by dividing a function of the cumulative friction work amount by the film thickness of the lubricating film and a second term of a function of the diffusion state; and determining a prediction of the occurrence of the adhesion of the metal particles to the die considering a result of the computing process.

3. The adhesion prediction method according to claim 1, wherein the cumulative friction work amount is calculated from a function obtained by integrating, over a forging time, a contact surface pressure, a friction coefficient, and a sliding velocity acting between the workpiece and the die for a minute time at each of element parts of the workpiece and the die.

4. The adhesion prediction method according to claim 1, wherein analysis of the diffusion state is performed by analyzing a diffusion amount of the metal particles using an Arrhenius equation in consideration of a combination of materials of the workpiece and the die and a processing temperature.

5. The adhesion prediction method according to claim 1, wherein the adhesion prediction determination step includes:
    performing a computing process of computing a product of a first term obtained by dividing a function of the cumulative friction work amount by the film thickness of the lubricating film and a second term of a function of the diffusion state; and
    determining a prediction of the occurrence of the adhesion of the metal particles to the die considering a result of the computing process,
    wherein the cumulative friction work amount is calculated from a function obtained by integrating, over a forging time, a contact surface pressure, a friction coefficient, and a sliding velocity acting between the workpiece and the die for a minute time at each of element parts of the workpiece and the die, and
    wherein analysis of the diffusion state is performed by analyzing a diffusion amount of the metal particles using an Arrhenius equation in consideration of a combination of materials of the workpiece and the die and a processing temperature.

6. The adhesion prediction method according to claim 1, wherein in the output step, an image information indicating the analysis model is generated, and the image information is output to an output device.

7. The adhesion prediction method according to claim 6, wherein the image information includes a group showing timings at which the adhesion is predicted to occur.

8. The adhesion prediction method according to claim 6, wherein the image information includes a mapping diagram of a processing shape of the workpiece.

9. The adhesion prediction method according to claim 8, wherein in the adhesion prediction determination step, values of an adhesion determination function are determined, and the mapping diagram indicates the values of the adhesion determination function in different colors by sections.

10. The adhesion prediction method according to claim 8, wherein in the adhesion prediction determination step, values of an adhesion determination function are determined, and the mapping diagram indicates the values of the adhesion determination function in different segments by a threshold value.

11. A non-transitory computer-readable storage medium storing an adhesion prediction program for predicting an adhesion of metal particles in a workpiece to a die in a forging process using an aluminum-based material as the workpiece, the adhesion prediction program causing a computer to execute:

an input process of receiving computer-aided design (CAD) information from a CAD device and various conditions that are used for analysis from an input device;

a cumulative friction work amount calculation process of calculating a cumulative friction work amount generated between the workpiece and the die;

a metal diffusion analysis process of analyzing a diffusion state of the metal particles between the workpiece and the die;

an adhesion prediction determination process of predicting a state of an occurrence of the adhesion of the metal particles to the die, considering the cumulative friction work amount calculated in the cumulative friction work amount calculation process, the diffusion state analyzed in the metal diffusion analysis process, and a film thickness of a lubricating film provided on a surface of the die that comes into contact with the workpiece, the metal particles being of the aluminum-based material; and outputting an analysis model of the occurrence of the adhesion.

12. An adhesion prediction device for predicting an adhesion of metal particles in a workpiece to a die in a forging process using an aluminum-based material as the workpiece, the adhesion prediction device comprising:

an input unit that receives computer-aided design (CAD) information from a CAD device and various conditions that are used for analysis from an input device;

a cumulative friction work amount calculation unit that calculates a cumulative friction work amount generated between the workpiece and the die;

a metal diffusion analysis unit that analyzes a diffusion state of the metal particles between the workpiece and the die; and an adhesion prediction determination unit that predicts an occurrence of the adhesion of the metal particles to the die, considering the cumulative friction work amount calculated by the cumulative friction work amount calculation unit, the diffusion state analyzed by the metal diffusion analysis unit, and a film thickness of a lubricating film provided on a surface of the die that comes into contact with the workpiece, the metal particles being of the aluminum-based material; and outputting an analysis model of the occurrence of the adhesion.

* * * * *